United States Patent [19]

Rasmussen

[11] 4,298,746
[45] Nov. 3, 1981

[54] N-(SUBSTITUTED PHENYL)-N'-(2-IMIDAZOLIDINYLIDENE)UREAS

[75] Inventor: Chris R. Rasmussen, Ambler, Pa.

[73] Assignee: McNeilab, Inc., Fort Washington, Pa.

[21] Appl. No.: 156,900

[22] Filed: Jun. 6, 1980

Related U.S. Application Data

[63] Continuation-in-part of Ser. No. 972,579, Dec. 22, 1978, Pat. No. 4,229,462.

[51] Int. Cl.³ .............................................. C07D 233/44
[52] U.S. Cl. .................................................... 548/315
[58] Field of Search ........................................... 548/315

[56] References Cited

U.S. PATENT DOCUMENTS 3,168,520  2/1965  Kleemann .......................... 548/315

OTHER PUBLICATIONS

Douglas, G., et al., *Arzneim.-Forsch.* 1978, 28(8), 1435–1441.
*Chemical Abstracts,* 90:48236s (1979) [Douglas, G., et al., *Arzneim.-Forsch.* 1978, 28(8), 1435–1441].
*Chemical Abstracts,* Chemical Substance Index, vol. 90, p. 6079cs (1979).

*Primary Examiner*—Richard A. Schwartz

[57] ABSTRACT

N-(Mono- and (di-substituted phenyl)-N'-(2-imidazolidinylidene)urea compounds and acid addition salts thereof are taught, which are useful as antihypertensive agents.

7 Claims, No Drawings

N-(SUBSTITUTED PHENYL)-N'-(2-IMIDAZOLIDINYLIDENE)UREAS

RELATED APPLICATION

This application is a continuation-in-part of application Ser. No. 972,579, filed Dec. 22, 1978, now U.S. Pat. No. 4,229,462.

FIELD OF INVENTION

This invention relates to certain novel compounds which are N-(substituted phenyl)-N'-(2-imidazolidinylidene)ureas.

PRIOR ART

Certain imidazolidine ureas are known in the art. Thus, in U.S. Pat. No. 3,168,520 imidazolidine ureas and hexahydropyrimidine ureas are taught. These compounds are taught to be useful as dye stabilizers. The patent specifically teaches 2-phenylcarbamyliminoimidazolidine which is N-(2-imidazolidinylidene)-N'-phenylurea. There is no teaching or suggestion in the patent, however, for the use of imidazolidineureas and hexahydropyrimidineureas as active ingredients in pharmaceutical compositions.

Some urea compounds have been disclosed to have certain pharmacological properties. Thus, U.S. Pat. No. 4,060,635 discloses amidinoureas. These compounds have an aryl group on one urea nitrogen and a substituted amidino group on the other urea nitrogen. U.S. Pat. Nos. 3,539,616 and 3,784,582 teach amidinoureas in which one urea nitrogen is substituted with an aryl group and the other urea nitrogen is substituted with an unsubstituted amidino group. None of the patents teaches or suggests the substitution of an imidazolidinylidene group on a urea nitrogen. None of these patents teaches or suggests anti-hypertensive activity. Recently, patents have issued claiming antihypertensive activity for these amidinoureas. Thus U.S. Pat. No. 4,088,785 is concerned with compounds having the structure

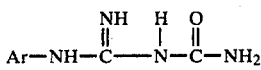

which is an opposite type of configuration from those of the instant invention. U.S. Pat. No. 4,117,165 is concerned with amidinoureas which have no substituents on the amidine nitrogen atoms, but are N-unsubstituted-amidine ureas, such as those having the struture

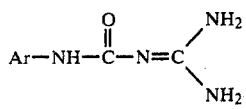

A recent publication, G. H. Douglas, et al., *Arz. Forsch/Drug Res.* 28(II), 1435 (1978) discloses the results of many aryl substituted amidinoureas screened for antimotility and antisecretory activity. N-(2,6-Dimethylphenyl)-N'-(2-imidazolidinylidene)urea and N-(2,6-dimethylphenyl)-N'-(1-methyl-2-imidazolidinylidene)urea are among the compounds tested. No other pharmacological test is reported or use suggested for these compounds.

DESCRIPTION OF THE INVENTION

This invention is concerned with novel chemical compounds which are N-(substituted phenyl)-N'-(2-imidazolidinylidene)ureas, having unexpected properties as antihypertensive agents (as shown in the parent application, Serial No. 972,579 now U.S. Pat. No. 4,229,462). These compounds have the structure:

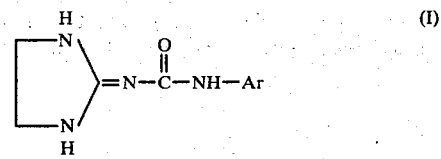

or a pharmaceutically-acceptable acid addition salt thereof. In the foregoing and subsequent formulas, Ar is phenyl substituted with one or two substituents independently selected from halo, such as fluoro, chloro and bromo; $C_1$-$C_2$ loweralkyl, such as methyl and ethyl; $C_1$-$C_2$ loweralkoxy such as methoxy and ethoxy, and trifluoromethyl.

In the most preferred compounds, Ar may be represented by

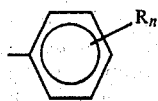

wherein R is methyl, chloro, bromo, or methoxy, and n is an integer from 1 to 2.

The activities of the above compounds reside in the urea base so that useful acid addition salts may be from various acids provided only that the acids be pharmaceutically-acceptable. Representative acid salts include hydrochloride, hydrobromide, phosphate, sulfate, p-toluenesulfonate, benzenesulfonate, methosulfate, methanesulfonate, ethanedisulfonic, 1- and 2-napsylate, and the like.

Although salts of I with weaker organic acids, such as benzoic, fumaric, maleic, citric, tartaric, pamoate, and the like do form, they are relatively easily dissociated because of the relatively weak base strength of I. This dissociation may be caused by attempted drying in vacuo, dissolution in $H_2O$, etc. This ease of dissociation, however, may not necessarily preclude their use in pharmaceutical formulations insofar as they remain stable enough to be purified by recrystallization, etc. and are capable of being formulated into pharmaceutical preparations, such as tablets, capsules, and the like.

Certain of the aforementioned salts have a propensity to form hydrates of varying composition. It is intended that said hydrates also be included within the scope of this invention.

The pharmacologically useful N-(substituted phenyl)-N'-(2-imidazolidinylidene)urea compounds are prepared by substantially two methods. The most generally useful method is by the reaction of an appropriate 2-iminoimidazoline (II) with an aryl isocyanate (III) according to the following equation:

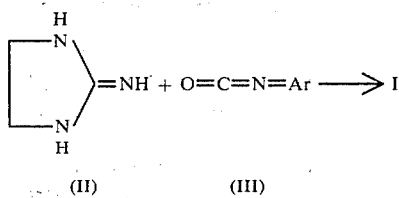

(II)    (III)

The 2-iminoimidazoline starting materials conveniently may be prepared (according to art methods and as subsequently described) and stored as an acid addition salt.

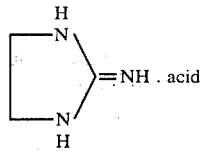

(IIa)

Thus, the initial step is usually the conversion of the acid addition salt IIa to the free base II. This may be carried out by thoroughly stirring a solution or suspension in tetrahydrofuran of the acid addition salt with two molar equivalents of 50 percent aqueous sodium hydroxide, followed by the addition of anhydrous sodium sulfate to remove excess water. The thus-obtained biphasic mixture is contacted with an appropriate aryl isocyanate to produce the desired N-(substituted phenyl)-N'-imidazolidinylideneurea compound.

In a preferred method for carrying out the reaction between the aryl isocyanate and the 2-imidazolidine, a solution of aryl isocyanate in tetrahydrofuran is added drop by drop with stirring to the biphasic mixture at temperatures in the range of about 20° to 30° C. and the mixture stirred for from a few hours to overnight. The N-(substituted phenyl)-N'-imidazolidinylideneurea compound thus obtained is recovered, converted to an acid addition salt form, if desired, and purified employing conventional procedures.

The free base may be generated by another procedure in which a solution of 2-iminoimidazolidine acid addition salt IIa is brought into contact with a suspension of lithium hydride, preferably, in the same solvent, under an inert atmosphere. Suitable solvents include dry dimethylformamide, dimethylsulfoxide, tetrahydrofuran, and the like. The temperature for addition is generally in the range of 0° to 30° C. An inert atmosphere is conveniently provided by use of nitrogen or argon.

In a preferred method for carrying out the reaction, a solution of 2-iminoimidazolidine acid addition salt IIa is added dropwise with stirring to a cooled suspension of lithium hydride in a dry solvent under nitrogen atmosphere while maintaining temperatures in the 0°–5° C. range. Stirring is continued after the completion of the addition while the mixture is gradually allowed to warm to room temperature to obtain the free base II.

The reaction between II and aryl isocyanate may be carried out by adding a solution of an aryl isocyanate, dropwise with stirring and cooling, to the reaction mixture containing the free base under at inert atmosphere, stirring the resulting mixture while gradually warming to ambient temperature and thereafter in the temperature range of from about 30° to 110° C., preferably in the range of 65° to 110° C. for optimizing yields, to obtain the desired N-(substituted phenyl)-N'-(2-imidazolidylidene)-urea product. When the reaction is carried our at ambient temperatures, stirring is usually continued for several hours or overnight; when it is carried out at the elevated temperatures, up to about two hours is generally satisfactory.

A second general but less preferred method for the preparation of N-(substituted phenyl)-N'-(2-imidazolidinylidene)urea compounds proceeds through the following sequence of reactions.

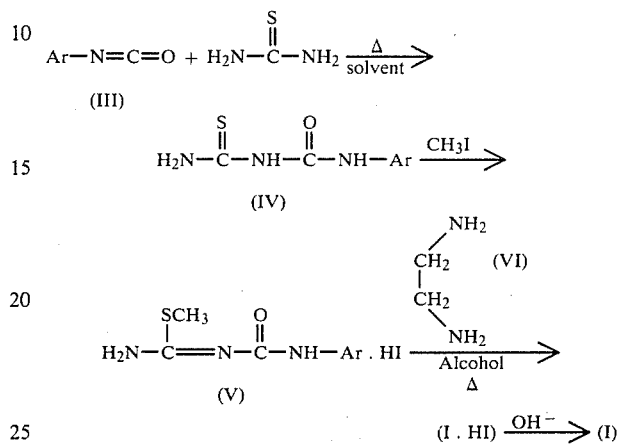

It is seen that the initial step is a reaction between an appropriate aryl isocyanate (III) and thiourea to produce an N-(substituted phenyl)-thioimidodicarbonicdiamide (IV) which is then reacted with methyl iodide to produce a methyl N'-[(arylamino)-carbonyl] carbamimidothioate (V). The latter when reacted with an appropriately substituted ethylenediamine (VI) produces the N-(substituted phenyl)-N'-(2-imidazolidinylidene)urea (I) as a hydroiodide addition salt and which may be converted to the free base by conventional means. The foregoing reaction sequence, however, does not appear to be applicable for the preparation of urea compounds in which the substituted phenyl group is a 2,6-disubstituted phenyl group.

The first step may be carried out employing a modification of a procedure reported by Lakra, et al., [J. Am. Chem. Soc. 51, 2220 (1929)] in which an appropriate substituted phenyl isocyanate (III) and thiourea are reacted to produce a N-(substituted phenyl)thioimidodicarbonic diamide compound (IV), hereinafter referred to for convenience as a "thiobiuret compound." For the reaction, substantially equimolar amounts of the reactants, preferably a slight excess of the thiourea, are employed. The temperature for the reaction may be in the range of from about 80° to 120° C. The reaction is preferably carried out in a solvent. Suitable solvents include dimethylformamide, dimethyl sulfoxide, and the like.

The reaction is preferably carried out by heating the isocyanate and thiourea at steam bath temperature for from about two to twelve hours whereupon the thiobiuret compound (IV) is formed in the reaction mixture. The mixture is then diluted with water and cooled to induce crystallization of the thiobiuret compound which is then separated from the reaction mixture and purified employing conventional procedures.

In the second step of the reaction, the N-(substituted phenyl)thiobiuret compound and an S-methylating agent are reacted to produce a methyl N'-[(substituted phenylamino)-carbonyl]carbamimidothioate compound (V), hereinafter referred to for convenience as the "thioate compound." Substantially equimolar amounts of the reactants, preferably a slight excess of methylating agent, are employed. Although other methylating agents such as dimethyl sulfate and the like also may be used, methyl iodide is preferred. A solvent is preferably employed. Suitable solvents include acetone, methanol, ethanol, isopropanol, and the like. The temperature of the reaction may range from ambient to reflux temperatures, ambient temperatures being preferred.

The reaction is conveniently carried out by mixing together the thiobiuret compound and methyl iodide in methanol at ambient temperature for several hours. The product which forms in the reaction mixture as its hydroiodide addition salt is recovered and purified, if desired, employing conventional procedures.

In the third step, the thioate compound (V) as the hydroiodide salt and an appropriate ethylenediamine compound (VI) are reacted to produce the desired N-(substituted phenyl)-N'-imidazolidinylideneurea product as a hydroiodide salt. Substantially equimolar amounts of the reactants are employed. The reaction is preferably carried out in methanol and other lower alkanols, methanol being preferred.

The reaction is conveniently carried out by refluxing together the hydroiodide salt of (V) and the ethylenediamine compound in methanol for from about one to several hours and thereafter vaporizing the solvent to obtain as residue the desired N-(substituted phenyl)-N'-imidazolidinylideneurea product as a hydroiodide salt. The product may then be recovered and purified employing conventional procedures.

The salt may be converted to the free base. If another salt is desired, the free base is caused to react with another acid to form a desired acid addition salt. Conventional procedures may be employed for these conversions. Thus, for example, a representative convenient procedure for obtaining the free base from the salt is dissolving the acid addition salt in a minimal amount of lower alkanol solvent such as methanol or ethanol, warming with an organic base such as triethylamine and the like, and cooling to obtain the free base product as a crystalline solid. Similarly, a representative convenient procedure for converting the free base to an acid addition salt is mixing the base with an alcoholic solution of an acid corresponding to the addition salt desired and cooling to obtain the acid addition salt.

The N-(substituted phenyl)-N'-(2-imidazolidinylidene)urea compounds of the present invention have been found to alleviate hypertension and further, to generally accomplish this without an accompanying increase in heart rate. The unsubstituted phenyl analogous prior art compound, N-(2-imidazolidinylidene)-N'-phenylurea, when tested, was found to be antihypertensive, but to have a short duration and to increase heart rate. The compounds of the present invention do not show an increase in heart rate, but a lowering of heart rate and, generally, longer duration. An agent which has an antihypertensive effect without increasing but rather maintaining or decreasing heart rate, is the one considered most useful for beneficially treating a hypertensive subject. The extent to which a compound possesses these properties may be primarily determined in the antihypertensive test hereinafter described.

Rodent Antihypertensive Screen—This test evaluates compounds for effects on arterial pressure and heart rate. In this test, the arterial pressure of adult spontaneously hypertensive rats (Charles River) is monitored directly via an aortic cannula. Rats are anesthetized with an inhalation anesthetic (methoxyflurane). The left carotid artery is isolated and cannulated. The tip of the cannula is advanced to the aorta and the cannula is exteriorized behind the neck at the level of the scapula. Animals are placed in individual cases and allowed to recover from the anesthetic and are kept unrestrained. The arterial cannula is connected to the pressure transducer which is attached to the recorder. Heart rate is determined from the arterial pressure recording. The test compounds are administered either orally (p.o.) by gavage or by intraperitoneal (i.p.) injection. The arterial pressure and heart rate are monitored for a minimum of 24 hours. A test compound is considered to be active as an antihypertensive agent if the mean arterial pressure (MAP) indicates a fall of >15 mm of Hg. Each animal serves as his own control. The results of this test employing at least 3 rats per dose level for each compound and performed with N-aryl-N'-(2-imidazolidinylidene)urea compounds are shown in Table I.

The results seen in Table I show that N-(substituted phenyl)-N'-(2-imidazolidinylidene)urea compounds and their salts possess not only the beneficial antihypertensive property but also the desirable property of maintaining or lowering heart rate.

The compounds of the present invention are useful for treating hypertension (high blood pressure) by administering to subjects in need of treatment, a therapeutically-effective hypertension reducing amount of a N-(substituted phenyl)-N'-(2-imidazolidinylidene)urea compound of Formula I or its pharmaceutically-acceptable salt as active agent. The active agents may be administered with or without carrier in the amounts hereinafter set forth. A preferred method of administration is by the use of pharmaceutical compositions in unit dosage form as described below.

The operable ranges for carrying out the treatment is the administration, orally or parenterally, of from about 5 milligrams to about 500 milligrams of said N-(substituted phenyl)-N'-(2-imidazolidinylidene)urea compound in dosage unit form. While the therapeutic method is most useful for human subjects, it may also be employed for other mammals. Operable amounts are generally within the range of from about 0.5 to 100 mg/kg of body weight.

TABLE I

ANTIHYPERTENSIVE AND CARDIAC RATE DETERMINATIONS

| Ar | McN | Dose mg/kg (Route) | Change in Mean Arterial Pressure (mm Hg) | Duration Hours | Change in Heart Rate Beats/min. |
|---|---|---|---|---|---|
| Ph (ART COMPD) | 4285-15 | 35 p.o. | −29 | 1 | +16* |
| 2,6-Cl$_2$Ph | 4335-11 | 35 p.o. | −48 to −64 | 27 | −64 to −78 |
| 2,6-Me$_2$Ph | 4355-11-98 | 35 p.o. | −48 | 3 | −68 |

TABLE I-continued
ANTIHYPERTENSIVE AND CARDIAC RATE DETERMINATIONS

| Ar | McN | Dose mg/kg (Route) | Change in Mean Arterial Pressure (mm Hg) | Duration Hours | Change in Heart Rate Beats/min. |
| --- | --- | --- | --- | --- | --- |
| 2,6-Br$_2$Ph | 4527-11 | 35 p.o. | −45 | 5 | −72 |
| 2-Cl-6-MePh | 4513-11 | 35 p.o. | −27 to −32 | 3-15 | −111 to −120 |
| 2-OMePh | 4562-11 | 10 p.o.** | −23 | Not Recorded | −84 |
|  |  | 100 p.o. | −84 | >4 | −90 |
| 2-MePh | 4822-11 | 35 p.o. | −34 | 5 | −31 |
| 2,3-Cl$_2$Ph | 4664-11 | 35 p.o. | −68 | 2 | −80 |
| 2-OEtPh | 4828-11-98 | 35 p.o. | −23 | 2 | −20 |

*1 experiments showed a decrease in heart rate (at 10 mg/kg p.o., MAP = −39 mm/Hg 9 hours duration and −108 beats/min). This one observation could not be substantiated also at 30 mg/kg i.p. and 100 mg/kg p.o., wherein heart rate was shown to be significantly INCREASED!
**35 mg/kg dose level was not performed.

Pharmaceutical compositions containing the N-(substituted phenyl)-N'-(2-imidazolidinylidene)urea compounds of the present invention or acid addition salt thereof, as the active ingredient, may be prepared by intimately mixing the urea compound with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed, including liquid carriers such as water, glycols, oils, alcohols and the like for oral liquid preparations such as suspensions, elixers and solutions; and solid carriers such as starches, sugars, kaolin, calcium stearate, ethyl cellulose, etc., including materials which function as lubricants, binders, disintegrating agents and the like for powders, capsules and tablets. Because of their ease in administration, tablets and capsules represent the most advantageous oral dosage form. These compositions employ solid pharmaceutical carriers such as the aforementioned starches, sugars, kaolin and the like, generally with a lubricant such as calcium stearate. It is especially advantageous to formulate the aforementioned pharmaceutical compositions in dosage unit form for ease of administration and uniformity of dosage. The term "dosage unit form" as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets, capsules, pills, powder packets, wafers, teaspoonful, tablespoonful and the like, and segregated multiples thereof. A dosage unit generally will contain from about 5 to about 500 mg of the N-(substituted phenyl)-N'-(2-imidazolidinylidene)urea compound.

The following examples illustrate the preparation of the N-(substituted phenyl)-N'-(2-imidazolidinylidene)urea compounds and the novel pharmaceutical compositions suitable in the practice of the invention but are not to be construed as limiting:

Starting Material—The 2-iminoimidazolidine starting material of Formula (IIa) may be prepared by literature-described methods or by the following representative preparation of the hydroiodide addition salt:

213 grams (1.5 moles) of methyl iodide is added with stirring over one hour to a suspension of 153.24 grams (1.5 moles) of ethylenethiourea in 300 milliliters of methanol. Stirring is continued for about an additional hour to complete the formation of S-methylethylenethiourea. Anhydrous ammonia then is added thereto whereupon a reaction takes place with the formation of 2-iminoimidazolidine hydroiodide and methylmercaptan by-product. The stirring and intermittent addition of ammonia is continued for a total of about 26 hours. The mixture is concentrated with concomitant addition of isopropanol to replace the vaporized methanol, and then cooled and ether added thereto to produce 2-iminoimidazoline hydroiodide as a crystalline solid which after recrystallization from methanol/tert.-butanol has a melting point of 152°–154° C.

Anal. Calcd. for C$_3$H$_7$N$_3$.HI; C, 16.92; H, 3.79
Found: C, 16.85; H, 3.82.

EXAMPLE I

N-(2,6-Dichlorophenyl)-N'-(2-imidazolidinylidene)urea Hydrochloride

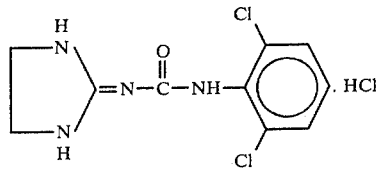

To a stirred suspension of 2.13 grams (0.01 mole) of 2-iminoimidazolidine hydroiodide in 50 milliliters of dry dimethylformamide under an atmosphere of nitrogen is added 0.8 gram (0.02 mole) of aqueous 50 percent sodium hydroxide to produce free 2-iminoimidazolidine base and sodium iodide. Thereafter, 1 gram of anhydrous sodium sulfate is added and the stirring continued for another one-half hour. To the mixture then is added dropwise over a 2.5 hour period, a solution of 0.94 gram (0.005 mole) of 2,6-dichlorophenyl isocyanate in 20 milliliters of tetrahydrofuran and the mixture allowed to stir overnight at room temperature to obtain a N-(2,6-dichlorophenyl)-N'-(2-imidazolidinylidene)urea product. The sodium salts are removed by filtration and the filtrate concentrated on a water bath under reduced pressure to obtain a pale yellow oil. The latter is dissolved in methylene chloride, and the methylene chloride solution first washed with saturated brine, dried over anhydrous potassium carbonate and treated with hydrogen chloride until pH<3 is reached. The solvent and excess hydrogen chloride are removed in vacuo and the residue recrystallized from methanol/ether to obtain purified N-(2,6-dichlorophenyl)-N'-(2-imidazolidinylidene)urea hydrochloride, m.p.

210°–212° C., which decomposes to a new solid which melts at 239° C.

EXAMPLE II

N-(2-Chloro-6-methylphenyl-N'-(2-imidazolidinylidene)urea and Hydrochloride

A solution of 10.65 grams (0.05 mole) of 2-iminoimidazolidine hydroiodide in dimethylformamide is added dropwise with stirring over a 15 minute period to a cooled to 5° C. suspension of 397.5 milligrams (0.05 mole) of lithium hydride in 50 milliliters of dry dimethylformamide under nitrogen whereupon hydrogen evolution is observed. While stirring is continued, the mixture is allowed to gradually warm to room temperature. Thereafter, the reaction mixture is cooled to 0°–5° C. and a solution of 5.0 grams (0.03 mole) of 2-chloro-6-methylphenyl isocyanate in 25 milliliters of dry dimethylformamide is added dropwise over a two hour period. After completion of the addition, the mixture is allowed to warm gradually to room temperature while the stirring under nitrogen atmosphere is continued overnight to obtain the desired N-(2-chloro-6-methylphenyl)-N'-(2-imidazolidinylidene)urea product which remains in solution. The product is recovered from the reaction mixture by (a) adding the mixture to 300 milliliters of ice water with stirring, (b) lowering the pH below 2 with aqueous 10 percent hydrochloric acid to precipitate acid insoluble material (c) filtering, (d) basifying the filtrate to pH 8–9 with solid potassium carbonate, and (e) saturating the solution with solid sodium chloride to precipitate the desired N-(2-chloro-6-methylphenyl)-N'-(2-imidazolidinylidene)urea free base as a white solid. The product after washing thoroughly with water has a melting point of 169°–171° C.

The product urea base is dissolved in 30 milliliters of methanol, and methanolic hydrogen chloride added thereto to a pH below 3. Ether is then added whereupon a N-(2-chloro-6-methylphenyl)-N'-(2-imidazolidinylidene)urea hydrochloride product precipitates. The latter is recovered and recrystallized successively from 2-propanol and methanol-ether to obtain a purified product, m.p. 209°–211°, which decomposes to a solid melting at 270° C. (dec.)

Anal. Calcd. for $C_{11}H_{13}ClN_4O\cdot HCL$: C, 45.69; H, 4.88; N, 19.37 Found: C, 45.59; H, 4.93; N, 19.35

EXAMPLE III

N-(2,6-Dibromophenyl)-N'-(2-imidazolidinylidene)urea Hydrochloride

In a manner similar to that described in Example II, a solution of 12.0 grams (0.0563 mole) of 2-iminoimidazolidine hydroiodide in 50 milliliters of dry dimethylformamide is added dropwise with cooling and under an atmosphere of nitrogen to a suspension of 447 milligrams (0.0563 mole) of lithium hydride in 50 milliliters of dry dimethylformamide. After completion of the addition the mixture is allowed to warm to room temperature over a period of about half an hour, then cooled to 0°–5° C., and a solution of 7.8 grams (0.0282 mole) of 2,6-dibromophenyl isocyanate in 25 milliliters of dry dimethylformamide is added dropwise over a two hour period while maintaining the cooled temperature range. The mixture is then allowed to warm to room temperature and stirred overnight under nitrogen to obtain the desired N-(2,6-dibromophenyl)-N'-(2-imidazolidinylidene)urea product in the reaction mixture. The product is recovered from the reaction mixture by pouring the mixture into 400 milliliters of ice water, acidifying with 10 percent hydrochloric acid to pH below 3, filtering to remove impurities, saturating the filtrate with solid sodium chloride and basifying with potassium carbonate to a pH of 8–9 to precipate the N-(2,6-dibromophenyl)-N'-(2-imidazolidinylidene)urea product as a white solid, m.p. 185°–190° C. (dec.).

The thus obtained base urea product is suspended in 40 milliliters of methanol and methanolic hydrogen chloride added thereto to a pH below 2. Ether is then added to precipitate the N-(2,6-dibromophenyl)-N'-(2-imidazolidinylidene)urea hydrochloride as a white solid, m.p. 200°–202° C. (dec.). After two recrystallizations from methanol/2-propanol/ether, there is obtained a purified product, m.p. 215°–217° C. decomposing to a solid, m.p. 255° C. (dec.).

Anal. Calcd. for $C_{10}H_{10}N_4Br_2O\cdot HCl$: C, 30.14; H, 2.78; N, 14.06 Found: C, 30.12; H, 2.81; N, 14.04

EXAMPLE IV

In a similar manner the following compound is prepared:

N-(2-Imidazolidinylidene)-N'-(2-methoxyphenyl)urea hydrochloride, m.p. 197°–199.5° C., by reacting 2-iminoimidazolidine (prepared from 2-iminoimidazolidine hydroiodide and lithium hydride) and 2-methoxyphenyl isocyanate at about 5° to 10° C. to obtain a N-(2-imidazolidinylidene)-N'-(2-methoxyphenyl)urea product, followed by reacting the urea base with methanolic hydrogen chloride and recrystallizing first from methanol/2-propanol, then twice from methanol ether.

Anal. Calcd. for $C_{11}H_{14}N_4O_2\cdot HCl$: C, 48.80; H, 5.58; N, 20.70 Found: C, 48.75; H, 5.61; N, 20.71

EXAMPLE V

In operations carried out in a manner similar to that described in Examples II–IV, the following compounds may be prepared:

N-(2,3-Dichlorophenyl)-N'-(2-imidazolidinylidene)urea and its hydrochloride, m.p. 218°–220° C.;

N-(2-Imidazolidinylidene)-N'-(2-methylphenyl)urea and its hydrochloride, m.p. 166°–168° C.;

N-(2,6-Dimethylphenyl)-N'-(2-imidazolidinylidene)urea and its hydrochloride hydrate, m.p. (210) 213°–216° C. dec;

N-(2-Chloro-6-trifluoromethylphenyl)-N'-(2-imidazolidinylidene)urea and acid addition salts thereof;

N-(2-Methyl-6-trifluoromethylphenyl)-N'-2-imidazolidinylidene)urea and acid addition salts thereof;

N-(2,6-bis-trifluoromethylphenyl)-N'-(2-imidazolidinylidene)urea and acid addition salts thereof;

N-(2-Methoxy-6-trifluoromethylphenly)-N'-(2-imidazolidinylidene)urea and acid addition salts thereof;

N-(2-Bromo-6-ethylphenyl)-N'-(2-imidazolidinylidene)urea and acid addition salts thereof;

N-(2-Bromo-6-chlorophenyl)-N'-(2-imidazolidinylidene)urea and acid addition salts thereof;

N-(2-Chloro-6-methoxyphenyl)-N'-(2-imidazolidinylidene)-urea and acid addition salts thereof.

I claim:

1. A compound selected from the group consisting of N-(2,6-dihalophenyl)-N'-(2-imidazolidinylidene)urea and pharmaceutically-acceptable salts thereof.

2. An N-(Substituted phenyl)-N'-(2-imidazolidinylidene)urea compound of the formula:

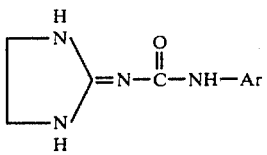

or a pharmaceutically-acceptable acid addition salt thereof, wherein Ar is phenyl substituted with one or two substituents independently selected from methyl, chloro, bromo or methoxy.

3. A compound of claim 1, which is N-(2,6-dichlorophenyl)-N'-(2-imidazolidinylidene)urea or a hydrochloride thereof.

4. A compound of claim 1, which is N-(2,6-dibromophenyl)-N'-(2-imidazolidinylidene)urea or a hydrochloride thereof.

5. A compound of claim 2, which is N-(2-chloro-6-methylphenyl)-N'-(2-imidazolidinylidene)urea or a hydrochloride thereof.

6. A compound of claim 2, which is N-(2,6-dimethylphenyl)-N'-(2-imidazolidinylidene)urea or a hydrochloride hydrate thereof.

7. A compound of claim 2, which is N-(2,3-dichlorophenyl)-N'-(2-imidazolidinylidene)urea or a hydrochloride thereof.

* * * * *